United States Patent [19]

Hohendorf et al.

[11] Patent Number: 5,259,841
[45] Date of Patent: Nov. 9, 1993

[54] SAFETY SYRINGE

[75] Inventors: Rainer Hohendorf, Pretoria; Willem H. Nel, Forest Hills, both of South Africa

[73] Assignee: Gemini Trade Overseas Ltd., Ramsey, Isle of Man

[21] Appl. No.: 840,495

[22] Filed: Feb. 24, 1992

[30] Foreign Application Priority Data

Feb. 25, 1991 [ZA] South Africa ............. 91/1339
Mar. 19, 1991 [ZA] South Africa ............. 91-2016
Jan. 30, 1992 [ZA] South Africa ............. 92/0675

[51] Int. Cl.$^5$ ........................... A61M 5/00
[52] U.S. Cl. ........................... 604/110; 604/198
[58] Field of Search ............ 604/198, 263, 110, 187, 604/192

[56] References Cited

U.S. PATENT DOCUMENTS

| | | | |
|---|---|---|---|
| 4,573,976 | 3/1986 | Sampson | 604/198 |
| 4,655,751 | 4/1987 | Harbaugh | 604/198 |
| 4,666,435 | 5/1987 | Braginetz | 604/198 |
| 4,737,144 | 4/1988 | Choksi | 604/198 |
| 4,846,796 | 7/1989 | Carrell et al. | 604/198 |
| 5,120,309 | 6/1992 | Watts | 604/110 |
| 5,120,311 | 6/1992 | Sagstetter et al. | 604/110 |
| 5,141,500 | 8/1992 | Hake | 604/198 |

FOREIGN PATENT DOCUMENTS

| | | |
|---|---|---|
| 0288879 | 11/1988 | European Pat. Off. |
| 0350186 | 1/1990 | European Pat. Off. |
| 0394537 | 10/1990 | European Pat. Off. |
| 2208604 | 12/1989 | United Kingdom |

*Primary Examiner*—John D. Yasko
*Attorney, Agent, or Firm*—Morgan & Finnegan

[57] ABSTRACT

A safety syringe 10 is disclosed and claimed. The syringe 10 comprises a tube 12 on which a hollow needle 16 is mountable for communicating with the inside of the tube. A plunger 28 is mounted in tube 12 for telescopic movement relative thereof. An outer sleeve 30 is mounted on the tube 12 and is moveable from a first needle - exposing position to a second needle covering position. Clips 40 are provided between tube 12 and sleeve 30 releasably to lock the sleeve in the said first position and permanently to lock the sleeve in the said second position. A formation 40.8 is provided on each clip on which pressure is exerted to release the clip when the sleeve is in its first position, without deformation of the sleeve.

13 Claims, 8 Drawing Sheets

SAFETY SYRINGE

INTRODUCTION AND BACKGROUND

This invention relates to syringes and more particularly to safety syringes of the kind comprising a telescopically moveable outer sleeve for covering a needle of the syringe, after use.

Various safety syringes of the kind referred to hereabove are known to the applicant. For example, in the specification of U.S. Pat. No. 4,655,751 to Harbaugh, there is disclosed such a safety syringe. The circular cylindrical sleeve of this syringe comprises a pair of integral, diametrically opposed and inwardly extending ears towards a rear end thereof. These ears, in use, co-operate with two pairs of opposed pockets defined respectively towards the rear and forward ends of a tube or barrel of the syringe. To release the ears from the rearward pockets, it is necessary to exert a force in a radially inwardly direction on the sleeve thereby to deform, more particularly, to oval the shape of the sleeve. This force must be exerted in opposed regions of the sleeve, spaced substantially ninety degrees from the ears. Finger grips are also provided on the sleeve in these regions.

The disadvantages of this syringe are that it is as easy to deform the sleeve and to release the ears from the pair of forward pockets and thereby to remove the sleeve from the tube, as it is to release the ears from the aforementioned rearward pockets. Thus, the sleeve is releasably locked in both its first and second positions. Furthermore, the ears and finger grips which are disposed at ninety degree intervals on the sleeve obscure the visibility of graduation marks on the tube of the syringe. Still furthermore, the pockets and channels defined in the outer surface of the tube require too drastic a departure from the know and conventional design of tubes or barrels for syringes.

OBJECT OF THE INVENTION

It is an object of the present invention to provide a syringe with which the applicant believes the aforementioned disadvantages will at least be alleviated.

SUMMARY OF THE INVENTION

According to the invention there is provided a syringe comprising:

a tube having a nozzle in a front end wall thereof and defining an opening at rear end thereof, a hollow needle being mountable on the tube to communicate with the nozzle;

a plunger mounted in the tube to extend through the opening and for telescopic movement relative to the tube;

the tube including a finger flange comprising two opposed finger grips positioned towards said rear end;

an outer sleeve having a rear end and a front end mounted coaxially with the tube to be moveable relative to the tube in telescopic manner from a first needle-exposing position to a second needle covering position;

locking means for releasably locking the sleeve in the first position and for permanently locking the sleeve in the second position;

means extending beyond the sleeve for releasing the locking means when the sleeve is in the first position; and the means for releasing the locking means being actuable by applying pressure in a radially inwardly direction thereon, thereby to release the locking means without deformation of the sleeve.

In this specification the term "permanently locked" is used to indicate that two parts are locked such that they cannot be disengaged without damage to the syringe as opposed to "releasably locked" which indicates that the parts may be disengaged from one another should the user so want, without any damage to the syringe.

The syringe preferably comprises at least one clip which is separate from both the tube and the sleeve and which is located between the tube and sleeve, the clip embodying at least part of the locking means and the means for releasing the locking means.

The clip may comprise a body, and the locking means may comprise a hook formation secured to the body to extend towards the rear end of the tube, releasably to co-operate with a finger flange at the rear end of the tube.

The finger flange includes two diametrically opposed finger grips. Each of the finger grips is axially in line with a corresponding locking means on the tube.

The clip preferably comprises a first radially outwardly extending formation on the body thereof for, in use, co-operating with a transverse hole defined in the sleeve thereby permanently to engage the sleeve.

Further according to the invention the clip may comprise two resiliently flexible curved arms extending in opposite directions away from the body of the clip to embrace partially and to abut against the tube thereby to define a clearance between the body of the clip and the tube to urge the said first radially outwardly extending formation into the transverse hole in the sleeve, thereby to engage the sleeve.

The means for releasing the locking means may comprise a second radially outwardly extending formation on the body of the clip. The said second radially outwardly extending formation being located beyond the rear end of the tube and also extending radially beyond the sleeve.

At least one hole may be defined in the finger flange through which the said hook formation, in use, extends to co-operate with the flange, when the sleeve is in its first position.

Further according to the invention the syringe may comprise guide means for preventing any rotational movement of the sleeve relative to the tube. The guide means preferably comprises an outwardly extending arrangement located towards the front end wall of the tube co-operating with at least one linear channel defined in an inside wall of the sleeve. The outwardly extending arrangement preferably comprises two pairs of spaced, radially outwardly extending lugs located in diametrically opposed regions on the tube co-operating with two linear channels defined in diametrically opposed regions in the sleeve.

Each of the pairs of outwardly extending lugs may define a channel between them. The locking means may further comprise an inwardly extending hook formation on the at least one clip for locking the sleeve in the second position; the inwardly extending hook formation being secured to the body of the at least one clip and having an elongate limb extending towards the front wall of the tube and a rearwardly and inwardly extending limb; the said inwardly extending hook formation locking the sleeve in its second position with the said elongate limb extending through the channel and the rearwardly and inwardly extending limb engaging the front end wall of the tube on one side of the pair of lugs. At the same time shoulder formations on the clip abut against an opposite side of the pair of lugs to prevent the sleeve from being removed from the tube.

In the preferred embodiment, the syringe comprises two clips located between the sleeve and tube, in diametrically opposed regions thereof.

Also according to the present invention there is provided a safety syringe comprising:

a transparent tube of circular cross section having a nozzle in a front end wall thereof and defining an opening at a rear end thereof, a hollow needle being mountable on the tube to communicate with the nozzle, the tube having graduation marks in a linear elongate region on an outer surface thereof;

a plunger mounted in the tube to extend through the opening and for telescopic movement relative to the tube;

an outer transparent sleeve of substantially circular cross section having a rear end and a front end mounted co-axially with the tube to be moveable relative to the tube in telescopic manner from a first needle - exposing position to a second needle - covering position;

guide means for preventing any rotational movement of the sleeve relative to the tube located in two diametrically opposed elongate regions of the syringe, substantially ninety degrees offset from the elongate region wherein the graduation marks are located;

locking means for releasably locking the sleeve in the first position and for permanently locking the sleeve in the second position, the locking means also being located in the said two diametrically opposed elongate regions so that the said linear elongate region wherein the graduation marks are provided, is not obscured by the guide means and the locking means.

Also included within the scope of the present invention is a medical instrument comprising:

a tube having a nozzle in a front end wall thereof and defining an opening at a rear end thereof, a hollow needle being mounted at the nozzle so that a first half thereof extends forwardly beyond the tube and a second half rearwardly and into the tube;

an evacuated cannister having a needle pierceable wall and which cannister is removably receivable in the tube;

an outer sleeve having a rear end and a front end mounted coaxially with the tube to be moveable relative to the tube in telescopic manner from a first position wherein the said first half of the needle is exposed to a second position wherein the said first half of the needle is covered;

locking means for releasably locking the sleeve in the first position and for permanently locking the sleeve in the second position; and means extending beyond the sleeve for releasing the locking means when the sleeve is in the first position;

the means for releasing the locking means being actuable by applying pressure in a radially inwardly direction thereon, thereby to release the locking means without deformation of the sleeve.

BRIEF DESCRIPTION OF THE DRAWINGS

The invention will now further be described, by way of example only, with reference to the accompanying diagrams wherein.

DESCRIPTION OF PREFERRED EMBODIMENT OF THE INVENTION

Figure 1:
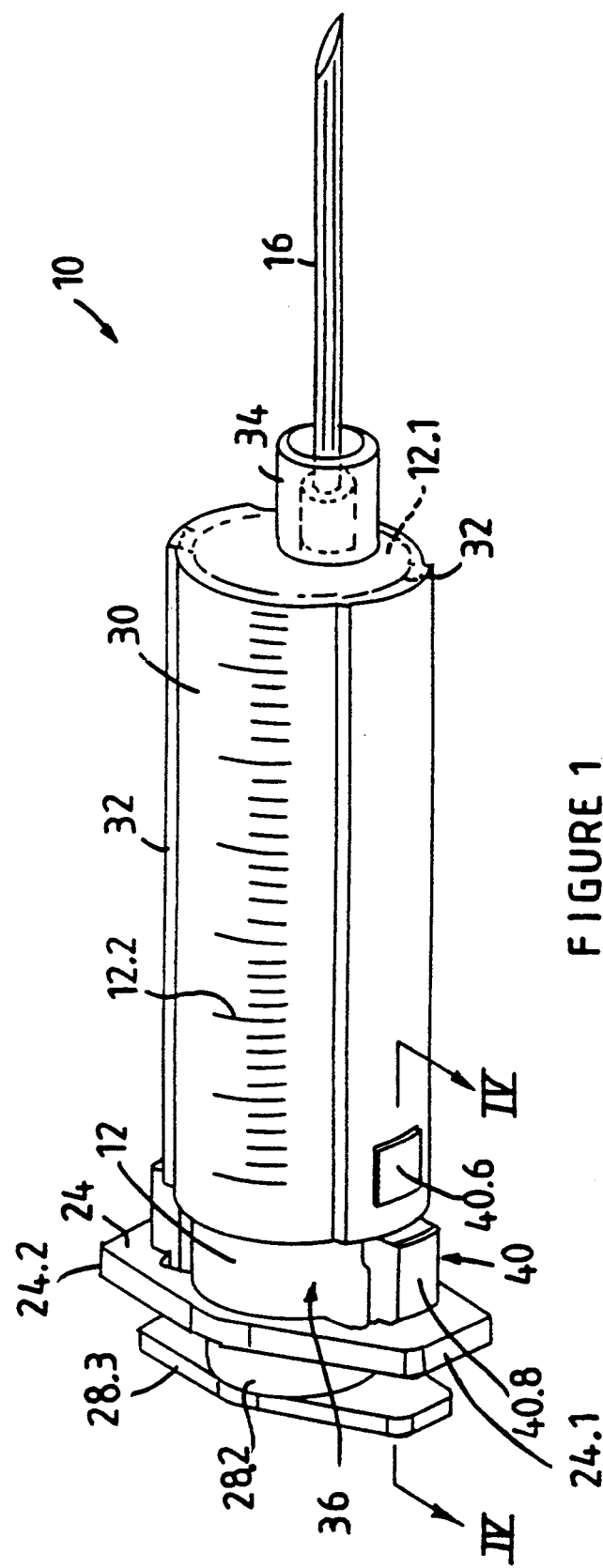
FIG. 1 is diagrammatic perspective view of a syringe according to the invention with a sleeve forming part of the syringe in a first, needle-exposing position.

A syringe according to the invention is generally designated by the reference numeral 10 in FIGS. 1, 2 and 3a–3d.

The syringe 10 comprises a transparent tube 12 of substantially circular transverse cross section. At one end of tube 12 there is provided an end wall 12.1 on which there is provided a nozzle 14. A hollow needle 16 is mountable on the nozzle to communicate with the inside of the tube. Also at the said one end of tube 12 there are provided two pairs of spaced outwardly projecting lugs 18 in diametrically opposed elongate and longitudinally extending regions on tube 12. Each pair of lugs 18 defines a channel 20 therebetween. At the other or rear end of tube 12 there is defined a mouth 22. An integral finger flange 21 including diametrically opposed finger grips 24.1 and 24.2 extends transversely to tube 12 at the said other end thereof. As is best shown in FIGS. 2, 3a, 3b, 4 and 5 opposed holes 26 are defined in flange 24 finger grips 24.1 and 24.2 immediately adjacent and radially outwardly from the aforementioned elongate regions on tube 12. Graduation marks 12.2 are provided on the tube 12. As best shown in FIGS. 3a, 3b and 3c, the graduation marks 12.2 are located in a linear elongate region offset by ninety degrees from the said elongate regions wherein the pairs of lugs 18 are located.

Figure 3A:
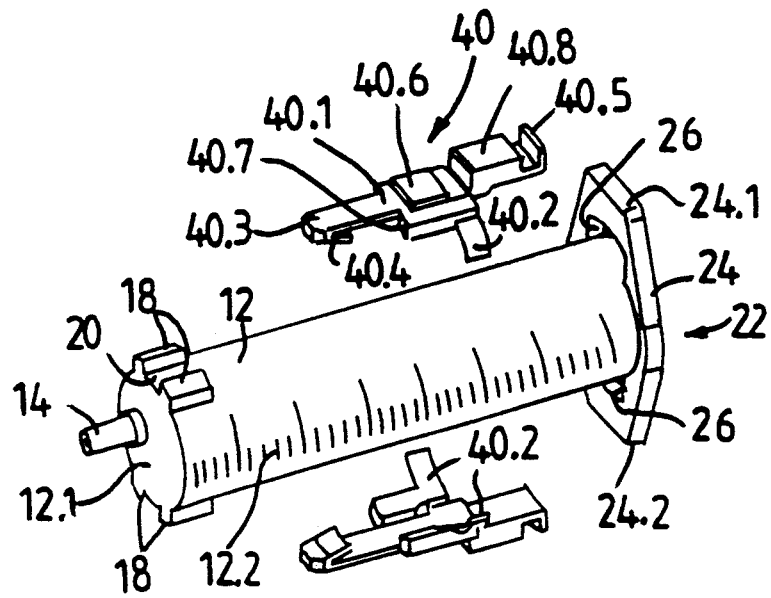
FIGS. 3a to d are diagrammatic perspective views illustrating how the syringe is assembled.
Figure 3B:
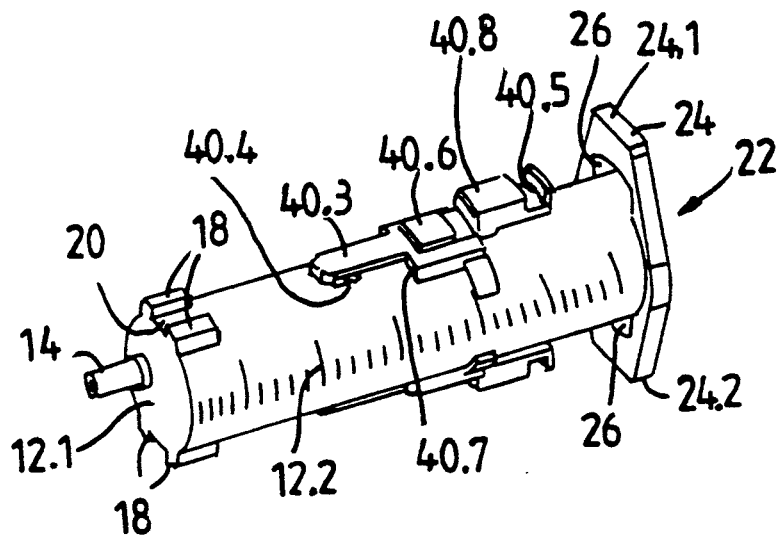
Figure 3C:
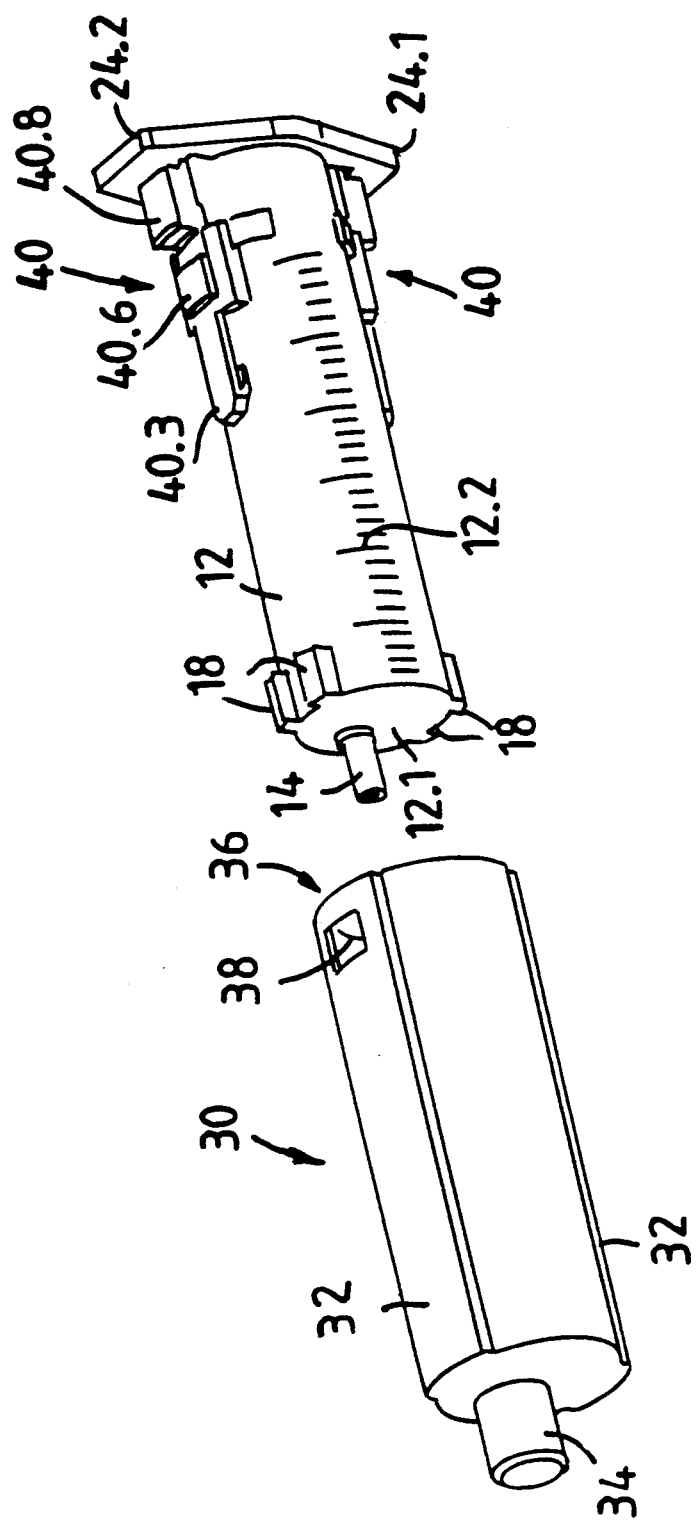
Figure 3D:
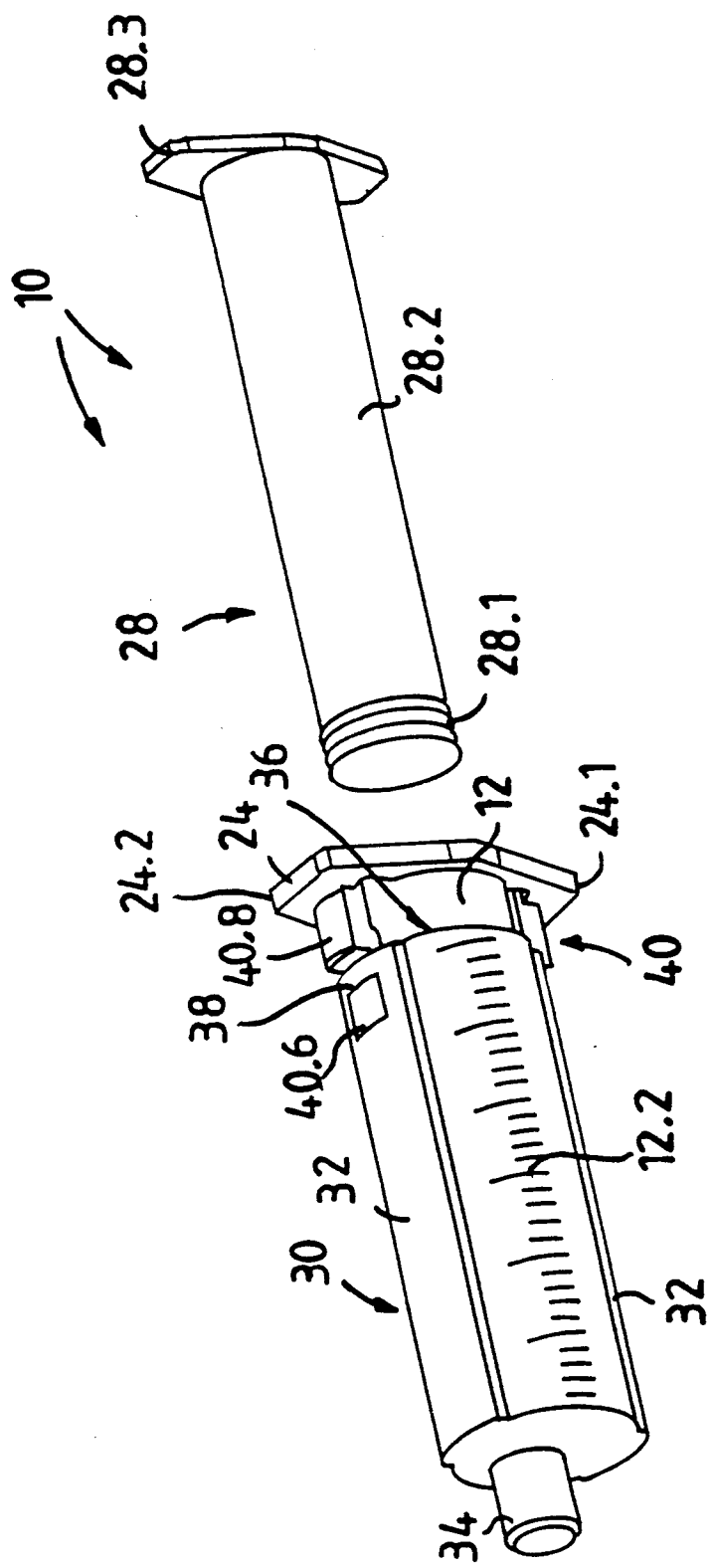

A plunger 28 is mounted in tube 12 and is moveable in telescopic fashion relative to tube 12—upon rearward movement to draw a fluid via needle 16 into the tube and upon forward movement to expel the fluid from the tube via nozzle 14 and needle 16. As is best shown in FIG. 3d, the plunger 28 comprises a piston 28.1 of a resiliently flexible material, a plunger stem 28.2 and a transverse flange 28.3.

Figure 2:
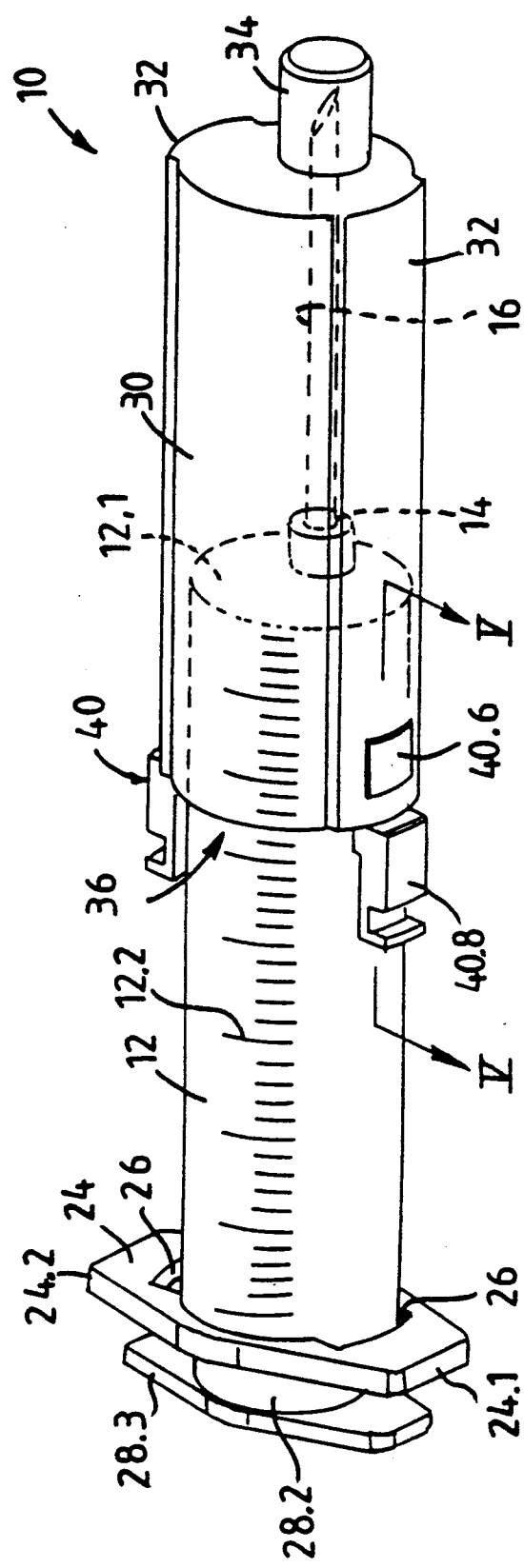
FIG. 2 is a similar view of the syringe with the sleeve in a needle-covering position.

The syringe further comprises a transparent sleeve 30 coaxially mounted on the tube 12 to move in telescopic fashion from a first, needle - exposing position (shown in FIG. 1) to a second, needle - covering position (shown in FIG. 2). Sleeve 30 comprises two internal channel defining formations 32 in diametrically opposed longitudinally extending elongate regions thereof. At one end of sleeve 30 there is provided a tubular neck 34 through which the needle extends, when the sleeve is in the first position. At the other end of sleeve 30 there is defined a mouth 36 through which the tube 12 extends. Also towards the other or rear end of the sleeve and in the channel defining formations 32, there are defined opposed transverse holes 38.

Between the tube 12 and sleeve 30 and partially in the channels defined by the formations 32, there is provided locking means in the form of two clips 40. As is best shown in FIGS. 3a, 3b and 3c, each clip comprises a body 40.1 and two transversely extending, curved arms 40.2.

Each clip 40, at one end of body 40.1, comprises an inwardly extending hook formation comprising an elongate member 40.3 and a radially inwardly extending limb 40.4. At the other end of the body 40.1 there is provided a radially outwardly extending hook formation 40.5. On the outer surface of each clip body 40.1 there is provided a first radially outwardly extending formation 40.6 for engaging sleeve 30 as will be described in more detail hereinafter. Elongate member 40.3 and body 40.1 provide two opposed shoulder formations 40.7, one on each side of the elongate member 40.3. Between the said first radially outwardly extending formation 40.6 and outwardly extending hook formation 40.5, there is provided means for releasing the locking means comprising a second radially outwardly extending formation 40.8.

As is best shown in FIGS. 1, 2, 3d, 4 and 5, clips 40 extend through the mouth 36 of sleeve 30 rearwardly towards the flange 24 on tube 12.

In FIGS. 3a to 3d the assembly of the syringe 10 according to the invention is illustrated. The first step is to mount clips 10 in diametrically opposed regions on tube 12 with the arms 40.2 partially embracing the tube 12 and so that elongate members 40.3 are located in the said longitudinally extending elongate regions on tube 12 and so that they may pass through channels 20. The clips are moved rearwardly towards flange 24 so that hook formations 40.5 extend through holes 26 and engage flange 24 on the other side thereof as tube 12, as shown in FIG. 4.

As shown in FIG. 3c, sleeve 30 is fitted onto tube 12 with lugs 18 received in the channels defined by formations 32. Sleeve 30 is moved towards flange 24 until formation 40.6 slip into transverse holes 38.

Figure 4:
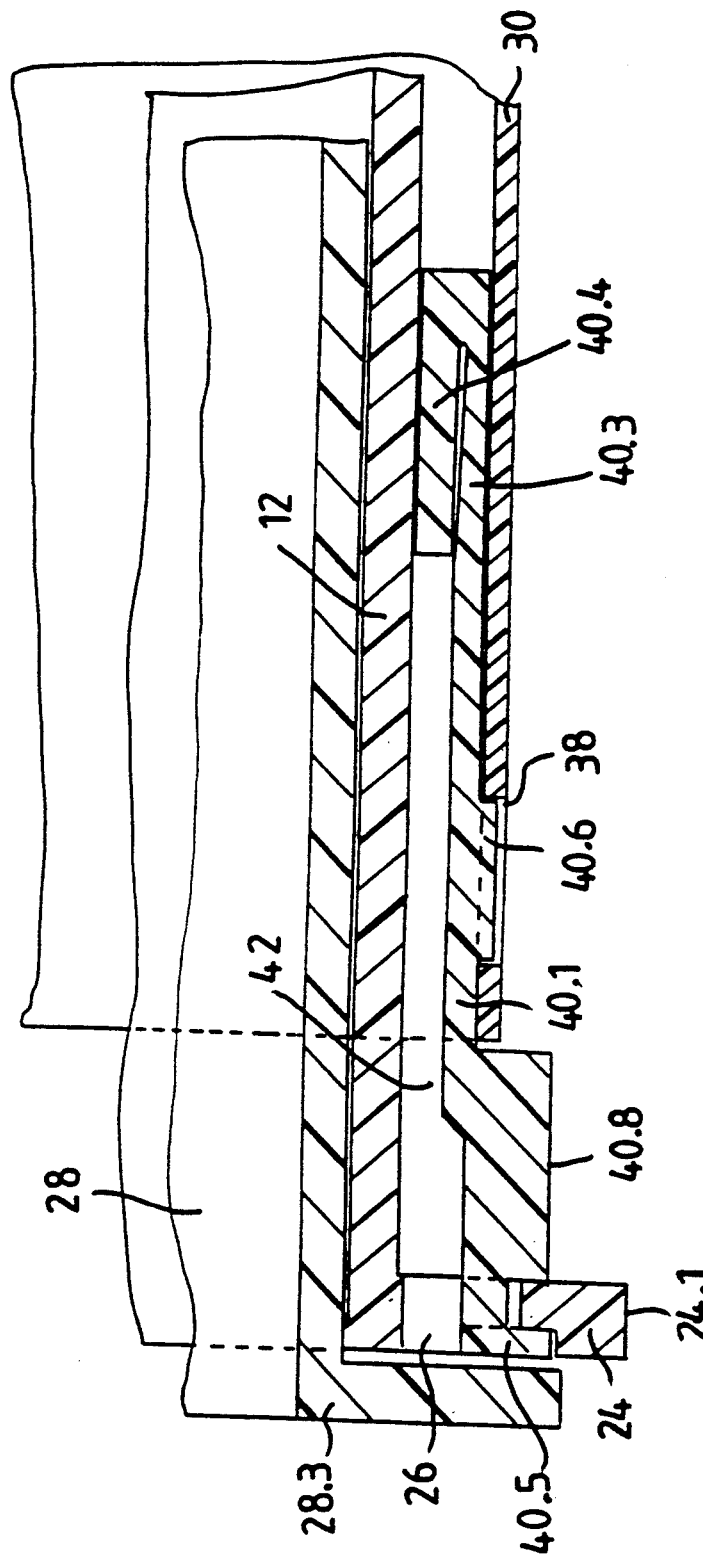
FIG. 4 is a section on line IV—IV in FIG. 1.

As shown in FIG. 4, with arms 40.2 (not shown in FIG. 4), abutting against the outer surface of tube 12, a clearance 42 is defined between the body 40.1 of clips 40 and the outer surface of the tube 12. The inwardly extending hook formations which are trapped in the channels defined by formations 32 are deformed so that the inwardly extending limbs 40.4 are urged towards elongate members 40.3. Arms 40.2 urge formations 40.6 into transverse holes 38 defined in formations 32, thereby permanently to engage the sleeve 30.

With hook formations 40.5 extending through holes 26 and engaging flange 24, finger grips 24.1 and 24.2 the sleeve 30 is releasably locked in its needle-exposing position.

After the syringe has been used, pressure is applied in a radially inwardly direction, on formations 40.8, thereby causing bodies 40.1 of the clips to move closer towards tube 12, so that hook formations 40.5 disengage flange 24.

Sleeve 30 with clips 40 are then moved towards the second position of the sleeve. The aforementioned opposed pairs of lugs 18, which fit in the channels defined by formations 32, act as guides to prevent any rotational movement of the sleeve 30 relative to tube 12.

Figure 5:
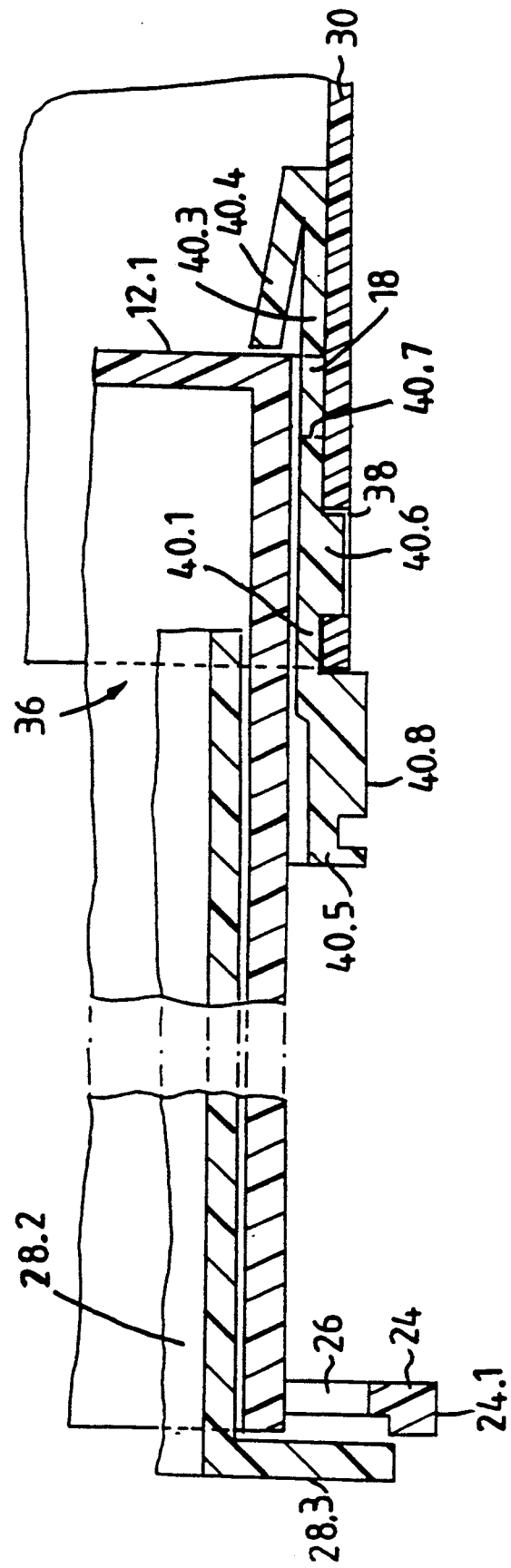
FIG. 5 is a section on line V—V in FIG. 2.

Elongate elements 40.3 and inwardly extending limbs 40.4 pass through the channels 20 defined by the pairs of lugs 18 and when the inwardly extending limbs reach the end wall 12.1 of the tube 12, they move, under the influence of their own resilience, to a position away from elongate member 40.3, thus abutting against the end wall 12.1 of the tube, as shown in FIG. 5. At the same time shoulder formations 40.7 abut against the ends of lugs 18 facing flange 24, so that they prevent the sleeve 30 from being removed from the tube 12.

The sleeve 30 is then permanently locked in its second and needle covering position.

After use, the complete syringe 10 is preferably disposed of.

It will be appreciated that one of the advantages of the syringe 10 according to the invention is that the sleeve 30 may be moved from its first needle-exposition position to its second position without any change of grip by the user of the syringe. More particularly, after the tube 12 has been filled with the liquid to be expelled from the syringe, the syringe is held with the middle and forefingers of one hand resting on formations 40.8 and the thumb of that hand on the flange 28.3 of plunger 28. The other hand supports the syringe by holding sleeve 30 in an intermediate region thereof. The liquid is expelled by urging the plunger 28 towards needle 16 by means of the aforementioned thumb.

After the fluid has been expelled, the sleeve 30 is released merely by urging the clips 40 inwardly by exerting pressure in a radially inward direction on formations 40.8, by means of the aforementioned middle and forefingers. The sleeve 30 is then moved towards its second position by the other hand still holding the sleeve as hereinbefore described. Thus, it is not necessary to remove the needle from the body injected with the liquid or to change grips, before the sleeve 30 is released.

Another important advantage of the syringe according to the invention is that the clips 40 and channel defining formations 32 are located in diametrically opposed regions of the syringe leaving the regions between these two opposed regions blank, so that the graduation marks 12.2 on the tube 12 are clearly visible through sleeve 30.

Yet another advantage is that the configuration of tube 12, apart from lugs 18, is substantially the same as that of many conventional syringe barrels. Thus, the tube may be made using current multi-cavity injection moulding techniques. In some cases, existing moulds may simply be reworked to accommodate the aforementioned difference.

Figure 6:
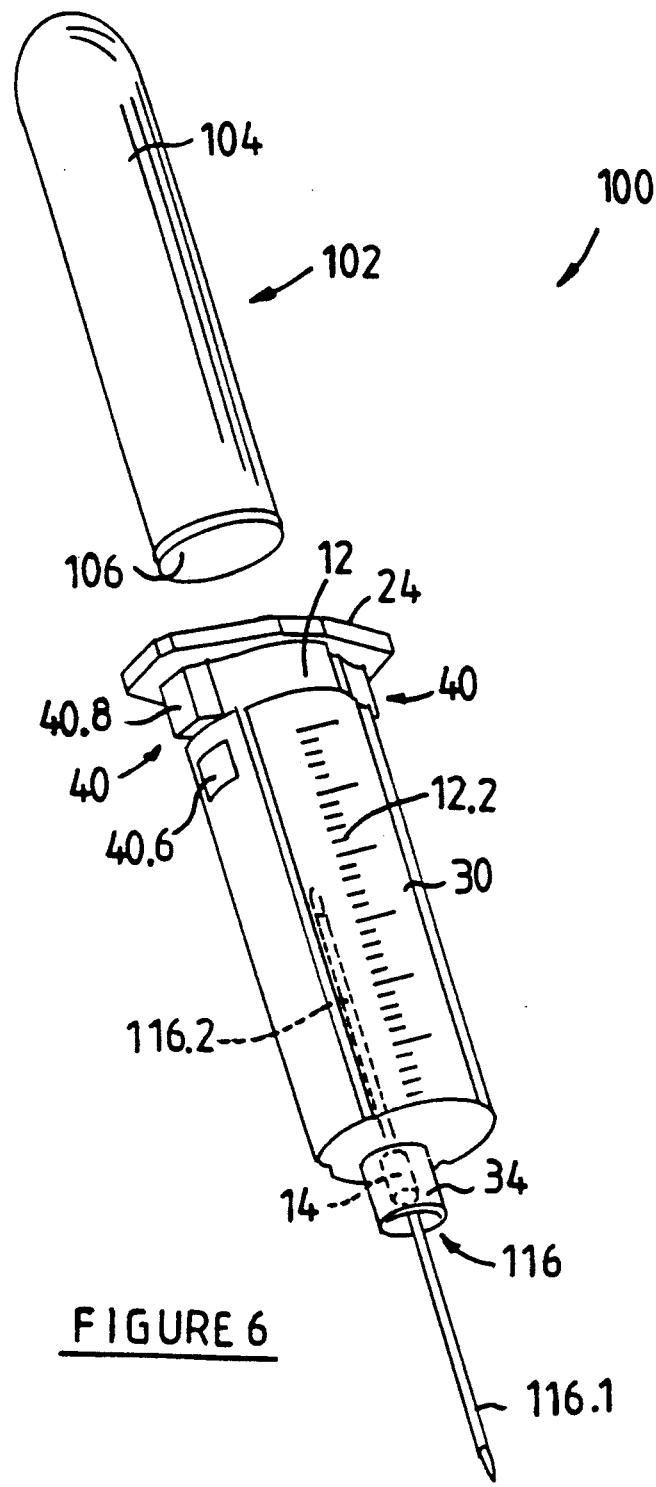
FIG. 6 is a diagrammatic partially exploded perspective view of a medical instrument according to the invention.

A medical instrument according to the invention for withdrawing a fluid, such as blood, from a body is generally designated by the reference numeral 100 in FIG. 6.

The instrument comprises a tube 12 and sleeve 30 similar to that of the syringe described hereinbefore. The sleeve 30 is also moveable from a first needle exposing position on tube 12 to be permanently locked in a second needle covering position by clips 40.

However, the instrument comprises a double needle 116 mounted in the nozzle 14 of the tube so that one half 116.1 thereof extends forwardly away from the tube and the other half 116.2 rearwardly into the tube.

Also forming part of the instrument 100 is an evacuated cannister 102 comprising a rigid tube 104 defining a blind bore. A needle pierceable membrane 106 covers an open end of the tube.

In use, needle half 116.1 of the instrument is inserted into the body from which the fluid is to be withdrawn. The cannister 102 is next inserted into tube 12 so that needle half 116.2 pierces the membrane 106. The vacuum inside the tube causes the fluid to flow from the body into cannister 102.

After the fluid sample has been withdrawn, the sleeve 30 is released and caused to move towards its second, needle covering position as hereinbefore described with reference to syringe 10. The cannister 102 with the fluid is then removed from the tube 12.

It will be appreciated that there are many variations in detail on the syringe according to the invention without departing from the scope and spirit of the appended claims.

We claim:

1. A syringe comprising:

a tube having a nozzle in a front end wall thereof and defining an opening at a rear end thereof, a hollow needle being mountable on the tube to communicate with the nozzle;

the tube including a finger flange comprising two opposed finger grips positioned towards said rear end;

a plunger mounted in the tube to extend through the opening and for telescopic movement relative to the tube;

an outer sleeve having a rear end and a front end mounted coaxially with the tube to be moveable relative to the tube in telescopic manner between a first needle-exposing position to a second needle-covering position;

locking means for releasably locking the sleeve in the first position and for permanently locking the sleeve in the second position; and means extending beyond the sleeve for releasing the locking means when the sleeve is in the first position, wherein with the sleeve in said first position, the means for releasing the locking means is located adjacent and axially in-line with at least one of said finger grips and actuable by applying pressure in an inwardly direction thereon, thereby releasing the locking means without deformation of the sleeve.

2. A syringe as claimed in claim 1 comprising at least one clip which is separate from both the tube and the sleeve and which is located between the tube and sleeve, the clip embodying at least part of the locking means and the means for releasing the locking means.

3. A syringe according to claim 2, wherein the clip comprises a body and the locking means comprises a hook formation secured to the body to extend towards the rear end of the tube to releasably co-operate with at least one of said finger grips.

4. A syringe according to claim 2 or claim 3, wherein the tube and sleeve are circular in transverse cross-section and the clip comprises a first radially outwardly extending formation on the body thereof for, in use, cooperation with a transverse hole defined in the sleeve, thereby permanently engaging the sleeve.

5. A syringe as claimed in claim 4 wherein the clip comprises two resiliently flexible curved arms extending in opposite directions from the body of the clip to embrace partially and to abut against the tube, thereby to define a clearance between the body of the clip and the tube and to urge the first radially outwardly extending formation into the transverse hole in the sleeve, to engage the sleeve.

6. A syringe as claimed in claim 4 or claim 5 wherein the means for releasing the locking means comprises a second radially outwardly extending formation on the body, the said second radially outwardly extending formation being located beyond the rear end of the sleeve and also extending radially beyond the sleeve.

7. A syringe claim 3, wherein a hole is defined in at least one of said finger grips through which said hook formation of at least one of said clips extends to co-operate with said at least one of said finger grips, when the sleeve is in its first position.

8. A syringe according to claim 2, further comprising guide means for preventing any rotational movement of the sleeve relative to the tube.

9. A syringe according to claim 8, wherein the guide means comprises an outwardly extending arrangement located towards the front end wall of the tube and axially in line with said at least one of said finger grips, the outwardly extending arrangement co-operating with at least one linear channel defined in an inside wall of the sleeve.

10. A syringe according to claim 9, wherein the tube and sleeve are circular in transverse cross-section and the outwardly extending arrangement comprises two pairs of diametrically opposed, radially outwardly extending lugs located axially in line with the two finger grips thereby co-operating with two linear channels defined in diametrically opposed regions in the sleeve.

11. A syringe according to claim 10, wherein each of the pairs of outwardly extending lugs defines a channel therebetween and the locking means further comprises an inwardly extending hook formation on the at least one clip for locking the sleeve in the second position; the inwardly extending hook formation being secured to the body of the at least one clip and having an elongate limb extending towards the front wall of the tube and a rearwardly and inwardly extending limb; said inwardly extending hook formation locking the sleeve in its second position with said elongate limb extending through the channel of one pair of said two pairs of lugs and the rearwardly and inwardly extending limb engaging the front end wall of the tube on one end of said one pair of lugs and shoulder formations on the clip abutting against an opposite end of said one pair of lugs.

12. A syringe according to claim 2, wherein the tube and sleeve are circular in transverse cross-section and further comprising two clips located between the sleeve and tube, in diametrically opposed regions thereof.

13. A medical instrument comprising:

a tube having a nozzle in a front end wall thereof and defining an opening at a rear end thereof, a hollow needle being mounted at the nozzle whereby a first half of said needle extends forwardly beyond the tube and a second half of said needle extends rearwardly into the tube;

the tube including a finger flange comprising two opposed finger grips positioned towards said rear end;

an evacuated canister having a needle pierceable wall and being removably receivable in the tube;

an outer sleeve having a rear end and a front end mounted coaxially with the tube to be moveable relative to the tube in telescopic manner from a first position wherein said first half of the needle is exposed, to a second position wherein said first half of the needle is covered;

locking means for releasably locking the sleeve in the first position and for permanently locking the sleeve in the second position; and means extending beyond the sleeve for releasing the locking means when the sleeve is in the first position;

wherein with the sleeve in said first position, the means for releasing the locking means is located adjacent and axially in line with at least one of said finger grips and actuable by applying pressure in an inwardly direction thereon, thereby releasing the locking means without deformation of the sleeve.

* * * * *